US00PP31684P2

(12) United States Plant Patent
NeSmith

(10) Patent No.: US PP31,684 P2
(45) Date of Patent: Apr. 21, 2020

(54) SOUTHERN HIGHBUSH BLUEBERRY PLANT NAMED 'TH-1876'

(50) Latin Name: *Vaccinium corymbosum*
Varietal Denomination: TH-1876

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,823

(22) Filed: Jan. 16, 2019

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

*Primary Examiner* — Susan McCormick Ewoldt
(74) *Attorney, Agent, or Firm* — Klarquist Sparkman LLP

(57) ABSTRACT

The new variety 'TH-1876' ripens around early May in southern Georgia. The fruit of the new variety 'TH-1876' are large, firm and have good flavor and scar. The new variety 'TH-1876' is vigorous with an estimated chilling requirement of about 300 to 350 hours at or below approximately 7° C. The asexually reproduced variety is reliably propagated vegetatively.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-1876' is a southern highbush blueberry plant that is a *Vaccinium corymbosum.*

Variety denomination: The new southern highbush blueberry plant claimed is of the variety denominated 'TH-1876'.

BACKGROUND OF THE INVENTION

The present invention relates to the discovery of a new and distinct cultivar of southern highbush blueberry plant botanically known as a *Vaccinium corymbosum* and herein referred to as 'TH-1876', as herein described and illustrated.

The new blueberry plant variety 'TH-1876' was selected in Griffin, Ga. in 2011. The new variety 'TH-1876' ripens around early May in southern Georgia. The fruit of the new variety 'TH-1876' are large with favorable firmness, scar, and good flavor. The new variety 'TH-1876' produces medium yield and has an estimated chilling requirement of about 300-350 hours at or below 7° C.

Pedigree and history: 'TH-1876' was selected in 2011 at Griffin, Ga., originating from seeds of open-pollinated 'Sweetcrisp' (U.S. Plant Pat. No. 20,027) fruit. 'TH-1876' was first asexually propagated at Griffin, Ga. in 2011 by vegetative cuttings. The selection has been tested in plantings at a research farm at Alapaha, Ga. since 2014.

Observations have shown that the unique features of this new *Vaccinium corymbosum* 'TH-1876' are stable and have reproduced true to type in successive generations.

SUMMARY OF THE INVENTION

The new blueberry plant variety 'TH-1876' has not been observed under all possible environmental conditions. The phenotype may vary somewhat with variations in environment and cultural practices, such as temperature and light intensity, without, however, any variance in genotype.

The following traits have been repeatedly observed in Alapaha, Ga. and are determined to be the unique characteristics of the new blueberry plant variety 'TH-1876':

1. Vigorous growth;
2. Favorable scar;
3. Good berry flavor; and
4. Favorable berry firmness.

The new variety 'TH-1876' can be compared to the southern highbush blueberry varieties 'Suziblue' (U.S. Plant Pat. No. 21,167) and 'Rebel' (U.S. Plant Pat. No. 18,138).

Comparison: The selection ripens with 'Suziblue' and 'Rebel' in the early Georgia southern highbush season. 'TH-1876' has large, firm berries with good flavor as compared to these standard blueberry varieties at Alapaha, Ga. over a 2-year period (Table 1). The chilling requirement is for 'TH-1876' is greater than for 'Sweetcrisp'.

TABLE 1

Table 1 sets forth two-year average ratings of some fruit and plant characteristics of 'TH-1876' and standard cultivars 'Suziblue' and 'Rebel' from 2016 and 2018 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2014.

| Berry and plant | Alapaha location | | |
|---|---|---|---|
| attributes | 'Suziblue' | 'Rebel' | 'TH-1876' |
| Berry size | 8.3 | 8.0 | 8.0 |
| Berry scar | 7.2 | 7.0 | 7.8 |
| Berry color | 7.2 | 7.0 | 7.5 |
| Berry firmness | 7.5 | 7.3 | 8.0 |
| Berry flavor | 7.0 | 6.5 | 7.5 |
| Cropping | 4.5 | 3.5 | 3.5 |

TABLE 1-continued

Table 1 sets forth two-year average ratings of some fruit and plant characteristics of 'TH-1876' and standard cultivars 'Suziblue' and 'Rebel' from 2016 and 2018 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2014.

| Berry and plant | Alapaha location | | |
|---|---|---|---|
| attributes | 'Suziblue' | 'Rebel' | 'TH-1876' |
| Plant vigor | 7.5 | 7.5 | 8.6 |
| Date of 50% flowering | Feb. 28 | Feb. 26 | Mar. 1 |
| Date of 50% ripening | May 4 | Apr. 30 | May 6 |
| Fruit development period (days) | 69 | 63 | 66 |

BRIEF DESCRIPTION OF THE FIGURES

The accompanying photographic illustrations show typical specimens in full color of the foliage, flowering, and fruit of the new variety 'TH-1876'. The colors are as nearly true as is reasonably possible in a color representation of this type.

BOTANICAL DESCRIPTION

Figure 1A:
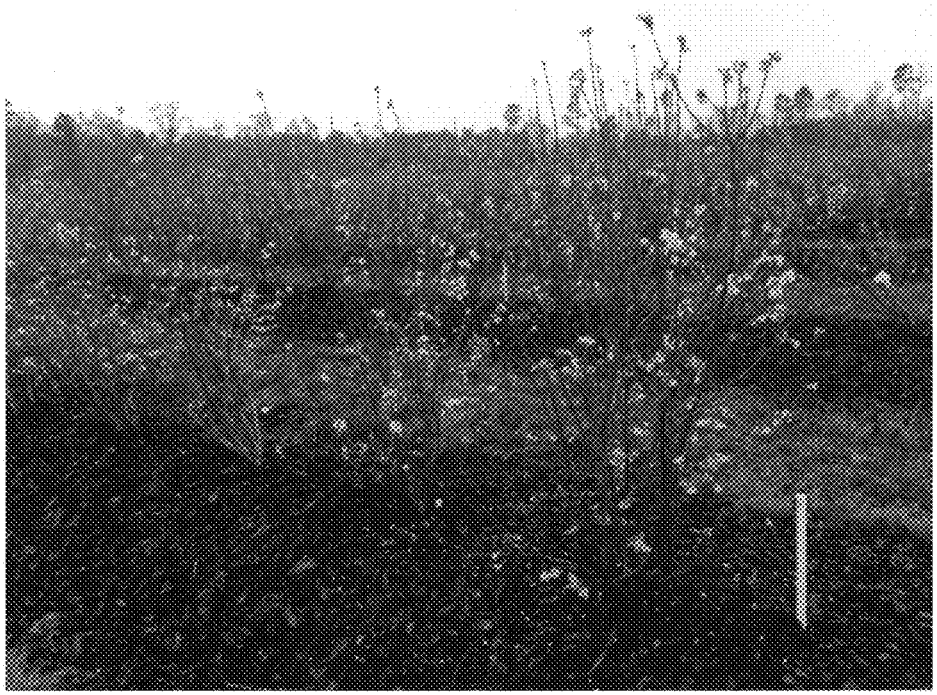
FIGS. 1A and 1B show photographs of the four year old plants of the new variety 'TH-1876' during flowering at Alapaha, Ga.
Figure 1B:
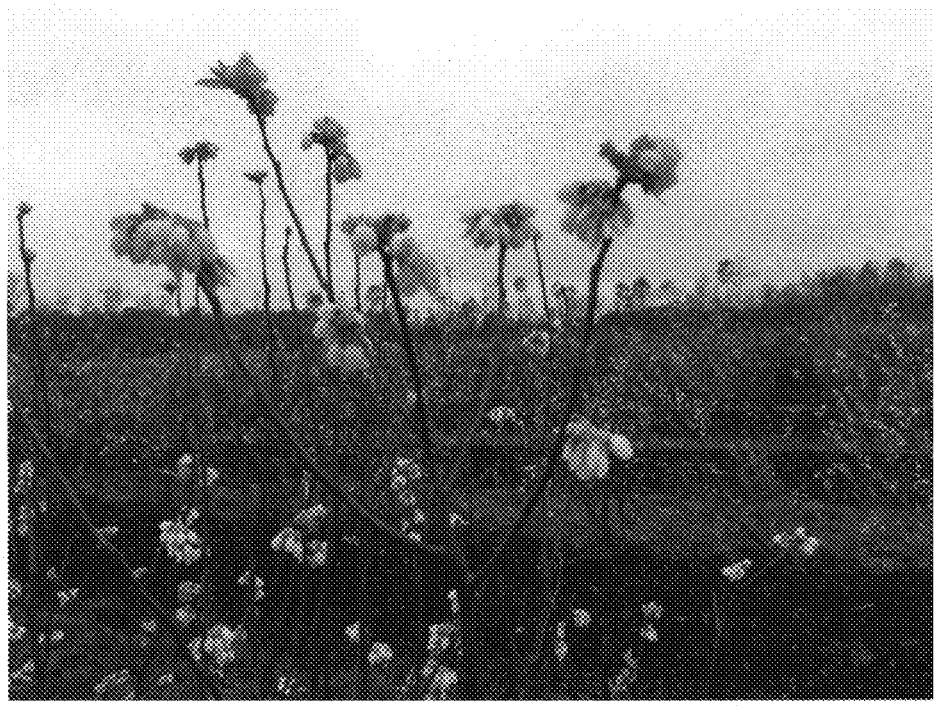
Figure 2:
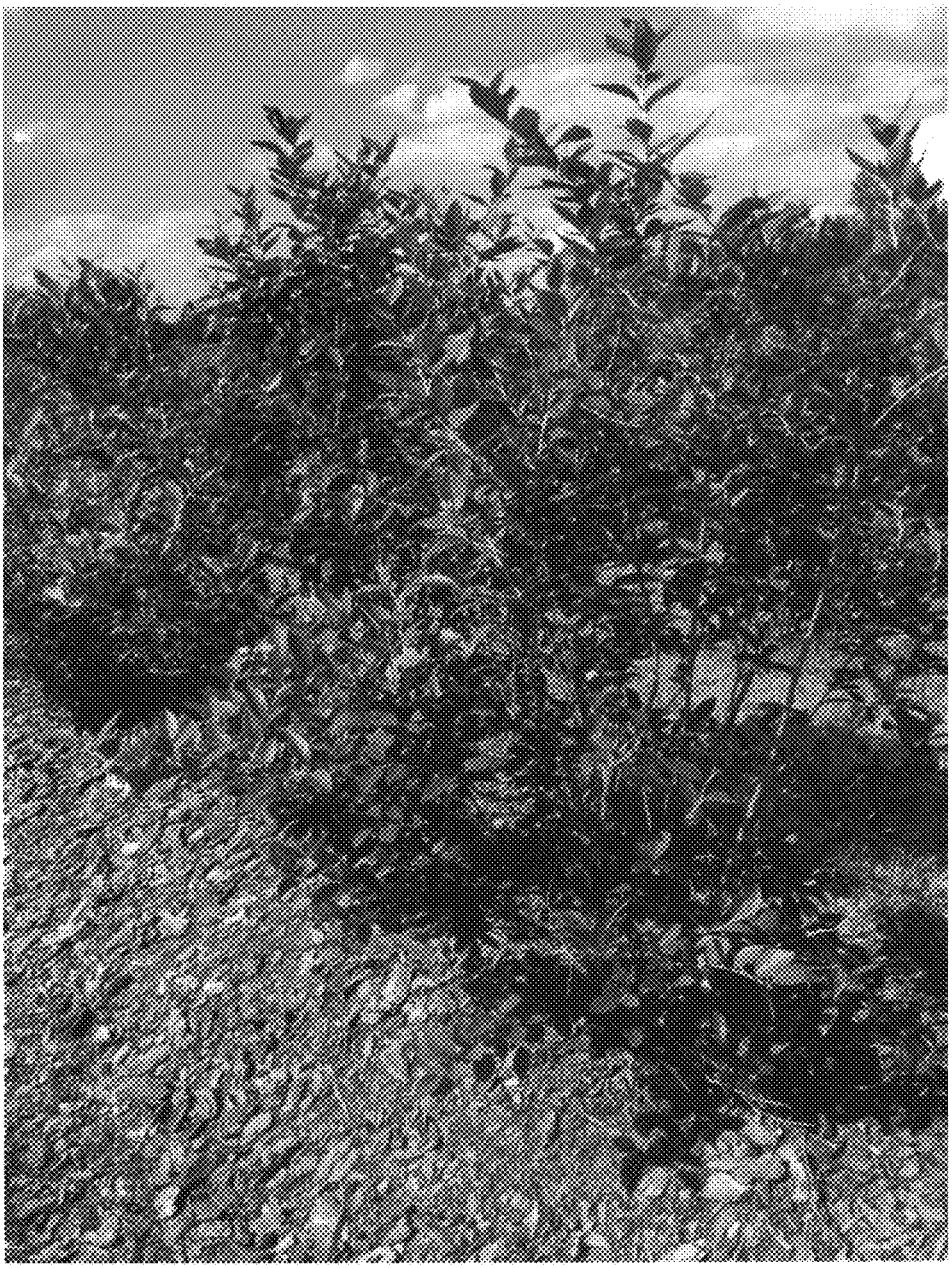
FIG. 2 is a photograph of four year old plants of the new variety 'TH-1876' at Alapaha, Ga.
Figure 3:
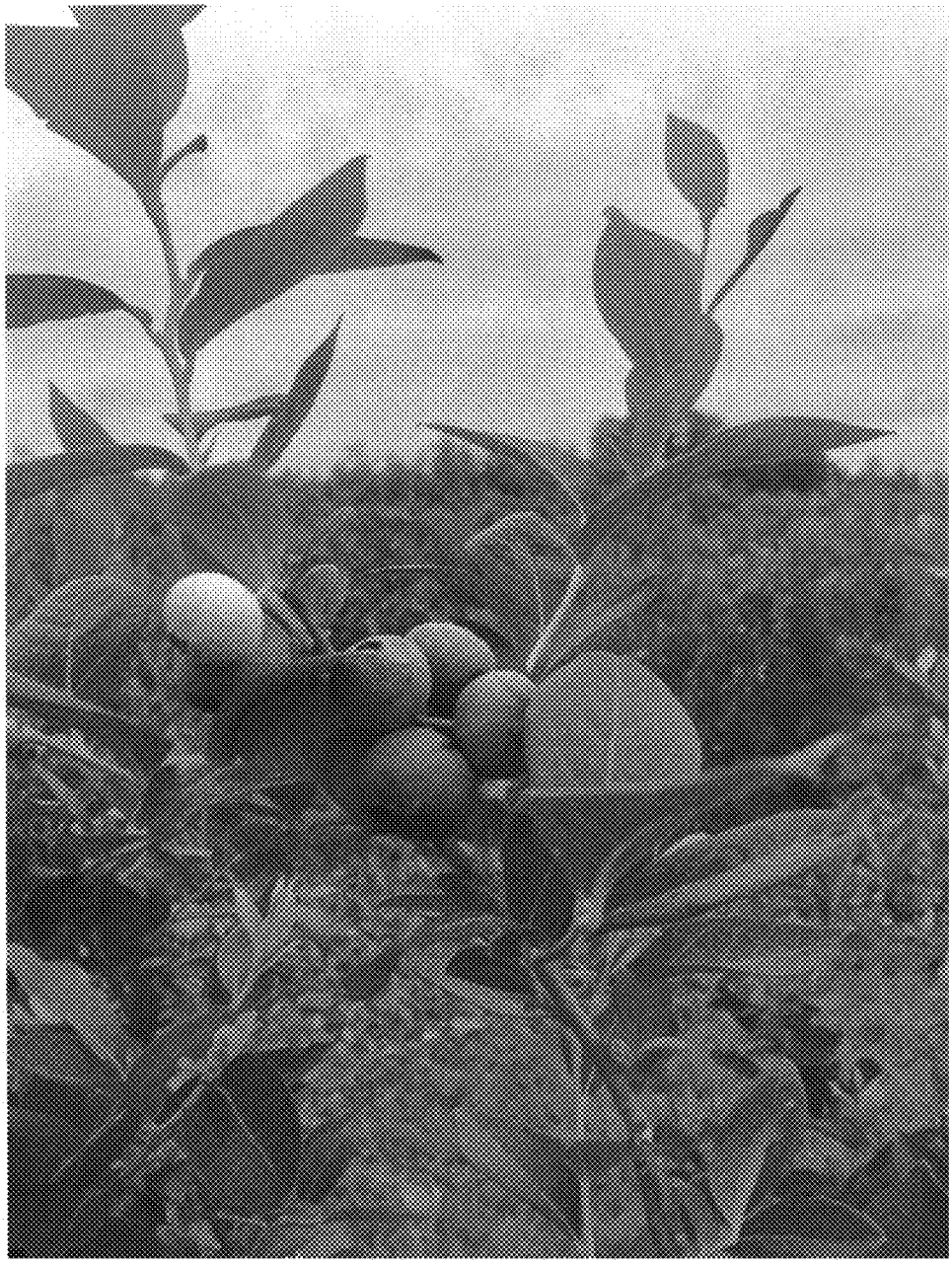
FIG. 3 is a close up photograph of a fruit cluster of the new variety 'TH-1876'.
Figure 4A:
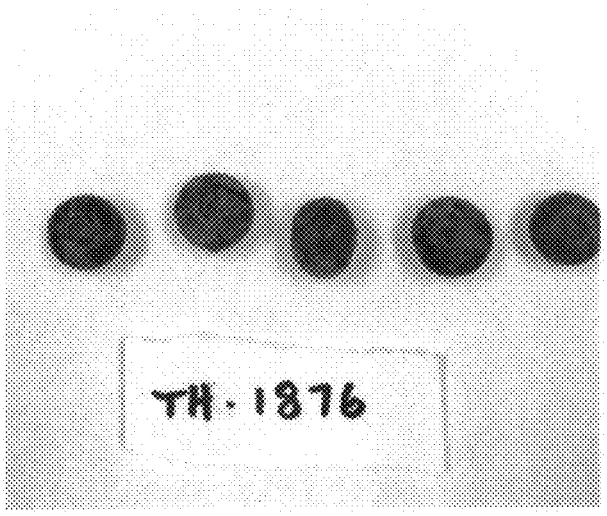
FIGS. 4A, 4B and 4C are photographs of harvested fruit of the new variety 'TH-1876'; with FIG. 4C depicting a bisected berry.
Figure 4B:
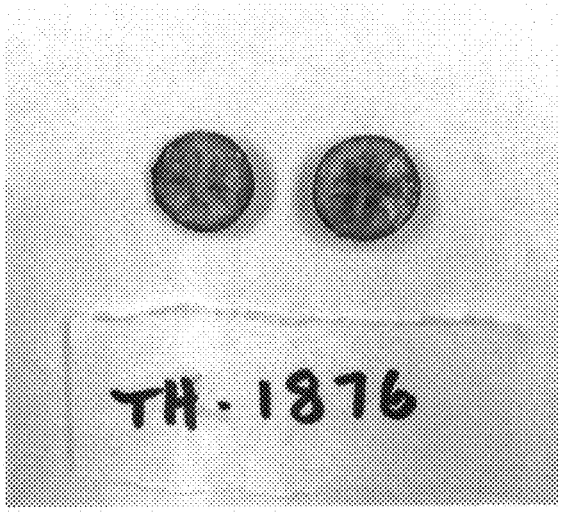
Figure 4C:
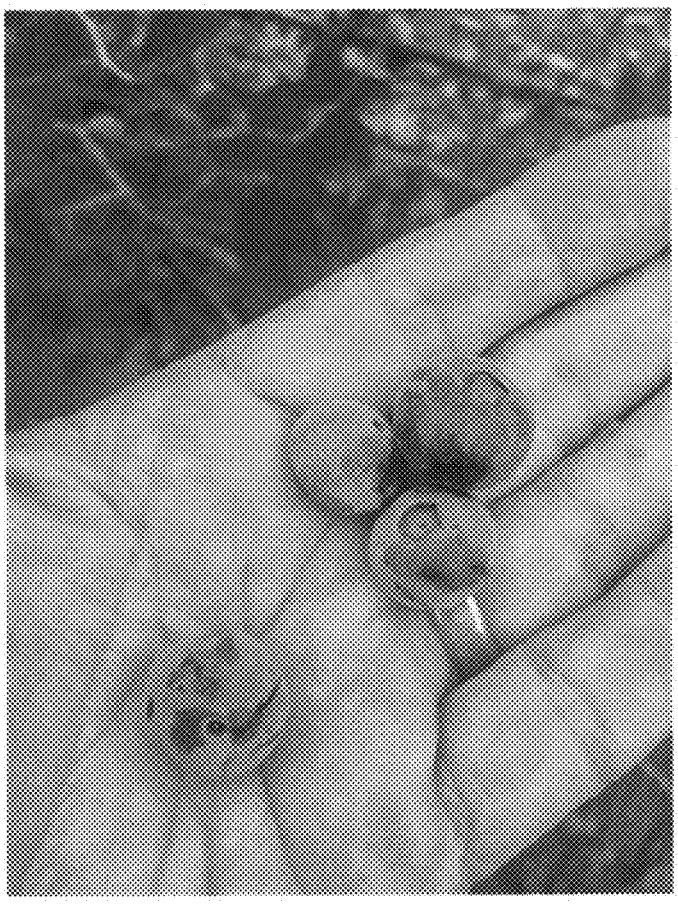

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'TH-1876'. Where dimensions, sizes, colors, and other characteristics are given, it is to be understood that such characteristics are approximations and averages set forth as accurately as practicable. The descriptions reported herein are largely from specimen plants grown in Alapaha, Ga with supplemental irrigation. Plants were about 3 to about 5 years old.

Plant:

*Size.*—1.2 to 1.5 m tall by 3 years. Plants grown under highly productive soil and fertility conditions can exceeded 1.5 m tall in 4 years. The plant crown, or base, is very narrow, typically 10 to 20 cm in diameter. Upper portion of the plant canopy reaches 0.8 to 1.2 m in diameter by 3 to 4 years.

*Growth habit.*—Plant is strongly upright and vertical, with 2 to 4 main canes arising from the crown, and quickly branching into multiple strongly vertical shoots from those canes 10 cm or less above ground.

*Growth.*—Plants are moderately vigorous.

*Productivity.*—Medium crop/yield. Yields of 4 to 6 lbs per plant each year on plants 3 to 4 years old grown under well-fertilized and irrigated field conditions.

*Hardiness.*—Although not tested except in portions of Georgia, the hardiness is believed to be similar to 'Suziblue' (U.S. Plant Pat. No. 21,167) and 'Rebel' (U.S. Plant Pat. No 18,138).

*Chilling requirement.*—Plants are medium chill, requiring only 300 to 350 hours, more or less, of temperatures at or below 7° C. to induce normal leafing and flowering during the spring under conventional dormant production systems. The chill requirement is greater than the female parent 'Sweetcrisp' (U.S. Plant Pat. No. 20,027; 100 to 250 hours of chilling required).

*Leafing.*—Plants tend to break sufficient leaf buds simultaneously with or shortly after anthesis.

*Canes.*—Diameter: Main cane base diameter 15 to 25 mm, two-year-old cane diameter 10 to 15 mm, current season wood diameter 5 to 10 mm. Color: Main cane color most near Brown RHS N200C; two-year-old cane color transitions from Yellow Green RHS 145A to Greyed Orange RHS 165B; current season wood color Yellow Green RHS 145A.

*Disease resistance.*—No exceptional disease resistance or susceptibility observed. Typical for early season southern highbush, such as 'Suziblue' and 'Rebel'.

Foliage:

*Leaf color.*—Healthy mature leaves. Top side: Green RHS 137B to RHS 137A. Under side: Yellow Green RHS 138C.

*Leaf arrangement.*—Alternate, simple.

*Leaf shape.*—Elliptic.

*Leaf surface.*—Glaucous, both upper and lower surfaces.

*Leaf margins.*—Entire.

*Leaf venation.*—Slightly to moderately reticulated.

*Leaf apices.*—Broadly acuminate to broadly acute.

*Leaf bases.*—Acute to nearly rounded.

*Leaf dimensions.*—Length: 75.0 to 85.0 mm. Width: 40.0 to 50.0 mm.

*Petioles.*—Small. Length: 5.0 to 7.0 mm. Width: 2.0 to 3.0 mm. Color: Yellow Green RHS 148C.

Flowers:

*Date of* 50% *anthesis.*—March 1 in southeast Georgia (2 year average).

*Flower shape.*—Urceolate.

*Flower bud number.*—Medium to high, averaging 5 to 7 buds per fruiting shoot.

*Flowers per cluster.*—6 to 9 common.

*Flower fragrance.*—None.

*Corolla tube.*—Color: White RHS 155C to White RHS NN155C (open flower). Length: 8.0 to 8.5 mm. Width: 6.5 to 7.5 mm. Aperture width: 2.5 to 3.5 mm.

*Flower peduncle.*—Length: 7.0 to 8.0 mm. Color: Yellow Green RHS 145C.

*Flower pedicle.*—Length: 3.0 to 4.0 mm. Color: Green RHS 139D.

*Calyx* (*with sepals*).—Diameter: 6.0 to 7.0 mm. Color: Green RHS 138B center, Green RHS 138C sepals.

*Stamen.*—Length: 7.0 to 7.5 mm. Number per flower: 10. Filament color: Yellow Green RHS 145D.

*Style*.—Length: 8.0 to 8.5 mm. Color: Green RHS 139D.

*Pistil*.—Length: 10.0 to 11.0 mm. Ovary color (exterior): Green RHS 138C to RHS 139D.

*Anther*.—Length: 4.0 to 4.5 mm. Number: 10. Color: Greyed Orange RHS 165B.

*Pollen*.—Abundance: Low to medium. Color: Yellow White RHS 158D.

*Self-compatibility*.—The cultivar has a moderate degree of self-compatibility.

Fruit:

*Date of* 50% *maturity*.—May 6 in southeast Georgia (2 year average).

*Fruit development period*.—66 days.

*Berry color*.—With wax: Blue RHS 100D. With wax removed: Black RHS 203C.

*Berry surface wax abundance*.—Medium to high.

*Berry flesh color*.—Green White RHS 157A.

*Berry weight*.—First harvest: 2.6 to 3.2 g. Second harvest: 1.6 to 2.3 g.

*Berry size*.—Height from calyx to scar: 15.0 to 18.0 mm. Diameter: 16.0 to 19.0 mm.

*Berry shape*.—Semi-spherical.

*Fruit stem scar*.—Very small to small, dry, with little or no tearing upon harvest.

*Calyx*.—Depth shallow, 1.0 to 2.0 mm; width medium, 5.0 to 7.0 mm; sepals typically not highly visible, flat or slightly erect when present, <<1 mm.

*Berry firmness*.—Very firm.

*Berry flavor and texture*.—Sweet, mild acidic flavor; crisp texture.

*Storage quality*.—Good to very good, berries remain firm and of high quality for up to 21 days under proper storage conditions.

*Suitability for mechanical harvesting*.—Likely suitable.

*Uses*.—Primarily to be used as fresh fruit for shipping and processing markets.

Seed:

*Seed abundance in fruit*.—Medium with 10 to 20 fully developed seeds per berry.

*Seed color*.—Greyed Orange RHS 164A.

*Seed dry weight*.—44.8 mg per 100 seed.

*Seed size*.—1.5 to 2.0 mm long.

What is claimed is:

1. A new and distinct variety of southern highbush blueberry plant named 'TH-1876', as illustrated and described herein.

* * * * *